(12) United States Patent
Welzig et al.

(10) Patent No.: US 8,212,029 B2
(45) Date of Patent: Jul. 3, 2012

(54) METHOD FOR THE PRODUCTION OF HIGH-PURITY 4A, 5, 9, 10, 11, 12,-HEXAHYDRO-6H-BENZOFURO [3A, 3, 2-EF] [2] BENZAZEPINE, AND THE DERIVATIVES THEREOF

(75) Inventors: Stefan Welzig, Vienna (AT); Anton Gerdenitsch, Rohrbach (AT); Jan Rothenburger, Oslip (AT); Susanne Kolar, Neufeld/Leitha (AT); Alexandra Scherleithner, Neufeld/Leitha (AT)

(73) Assignee: Sanochemia Pharmazeutika AG, Vienna (AT)

( * ) Notice: Subject to any disclaimer, the term of this patent is extended or adjusted under 35 U.S.C. 154(b) by 415 days.

(21) Appl. No.: 12/522,323

(22) PCT Filed: Feb. 14, 2008

(86) PCT No.: PCT/AT2008/000050
§ 371 (c)(1),
(2), (4) Date: Jul. 7, 2009

(87) PCT Pub. No.: WO2008/101266
PCT Pub. Date: Aug. 28, 2008

(65) Prior Publication Data
US 2010/0105895 A1    Apr. 29, 2010

(30) Foreign Application Priority Data
Feb. 22, 2007 (AT) .................. A 280/2007

(51) Int. Cl.
*A61P 25/28* (2006.01)
*A61K 31/55* (2006.01)
*C07D 491/10* (2006.01)

(52) U.S. Cl. ................................ 540/581

(58) Field of Classification Search .......... 540/581
See application file for complete search history.

(56) References Cited

FOREIGN PATENT DOCUMENTS

| GB | 2 247 890 A | 3/1992 |
|---|---|---|
| JP | 2000-119762 A | 4/2000 |
| WO | WO 96/12692 A1 | 5/1996 |
| WO | WO 97/11077 | 3/1997 |

OTHER PUBLICATIONS

Austrian Search Report, dated Oct. 15, 2007.
English-language Abstract of JP 55-043060 B, dated Nov. 4, 1980.
International Search Report dated Jun. 20, 2008.
Wen-Chung Shieh et al., "Asymmetric Transformation of Either Enantiomer of Narwedine via Total Spontaneous Resolution Process, a Concise Solution to the Synthesis of (−)-Galanthamine", J. Org. Chem., 1994, pp. 5463-5465, vol. 59, American Chemical Society.
Laszlo Czollner et al., "New Kilogram-Synthesis of the Anti-Alzheimer Drug (−)-Galanthamine", Tetrahedron Letters, 1998, pp. 2087-2088, vol. 39, Elsevier Science Ltd.
Chaplin, David, Fraser, Neil, and Tiffin, Peter, A Concise, Scaleable Synthesis of Narwedine, Teirahedron Letters, 1991, pp. 7931-7932, vol. 38, No. 45, Elsevier Science Ltd, Great Britain.

*Primary Examiner* — Brenda Coleman
(74) *Attorney, Agent, or Firm* — Young & Thompson

(57) ABSTRACT

A process for the production of extremely pure galanthamine and galanthamine derivatives is provided. Racemic bromine narwedine is debrominated under palladium catalysis. The reaction mixture is then worked-up in the presence of oxygen or peroxides so that the palladium catalyst is converted into an insoluble form that can be easily separated. Further reaction is carried out by reduction of enantiomerically pure narwedine to form enantiomerically pure galanthamine, which is then alkylated or dealkylated, so that a corresponding substitution on the ring-nitrogen atom is achieved. By further purification, such as recrystallization, residual portions of palladium of below 5 ppm are achieved. The pure galanthamine can then be directly used as a pharmaceutical raw material.

22 Claims, No Drawings

METHOD FOR THE PRODUCTION OF HIGH-PURITY 4A, 5, 9, 10, 11, 12,-HEXAHYDRO-6H-BENZOFURO [3A, 3, 2-EF] [2] BENZAZEPINE, AND THE DERIVATIVES THEREOF

FIELD OF THE INVENTION

The invention relates to a process for the production of extremely pure 4a,5,9,10,11,12-hexahydro-6H-benzofuro [3a,3,2-ef][2]benzazepine as well as its derivatives with the general formulas I and II

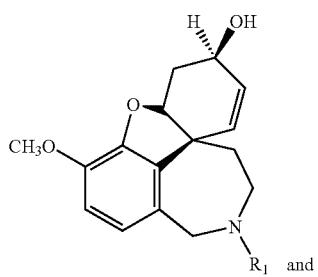

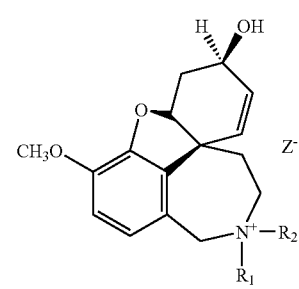

or salts thereof, in which $R_1$ is selected from the group that consists of hydrogen, hydroxy, alkoxy, low alkyl, which optionally is substituted by at least one halogen, low alkenyl, low alkinyl, aryl, aralkyl, aryloxyalkyl, formyl, alkylcarbonyl, arylcarbonyl, aralkylcarbonyl, alkyloxycarbonyl, aryloxycarbonyl, aralkyloxycarbonyl, alkylsulfonyl, aralkylsulfonyl, arylsulfonyl, and in which $R_2$ is selected from the group that consists of hydrogen, formyl, alkyl, alkenyl, aryl, aralkyl, alkylcarbonyl, arylcarbonyl, aralkylcarbonyl, alkyloxycarbonyl, aryloxycarbonyl, aralkyloxycarbonyl, alkylsulfonyl, arylsulfonyl and aralkylsulfonyl and whereby $Z''$ is an anion of a pharmaceutically acceptable organic acid or an inorganic anion.

BACKGROUND OF THE INVENTION

Galanthamine is an alkaloid with high pharmacological activity that primarily occurs in Amaryllidaceae-type plants. In particular, its action as a more selective acetylcholinesterase inhibitor and the thus associated application in the treatment of neurodegenerative diseases, such as Alzheimer's disease, are to be emphasized. The amounts isolated from the naturally occurring Caucasian snowdrop *Galanthus woronoyi* are not sufficient, however, to cover the requirement of a pharmaceutical raw material. Since the end of the 1960s, galanthamine syntheses have therefore been known that occasionally show long and uneconomical reaction routes with poor total yields, however.

According to WO-A-97/110777, a more economical route for the galanthamine synthesis is to be provided by a specific selection of bromine narwedine as a starting product since bromine narwedine is debrominated with palladium (II) acetate with the addition of triphenylphosphine. The racemic narwedine that is obtained contains about 700-800 ppm of palladium, however, which also cannot be separated after repeated treatment with activated carbon. Even in the case of additional reaction steps, such as the reduction of racemic narwedine, which is described according to WO-A-96/12692 of the applicant, palladium is further detected in the reaction end product despite repeated working-up.

Galanthamine or galanthamine derivatives, which have palladium in a measure of 700-800 ppm, are not suitable, however, for the production of pharmaceutical agents, such as agents for treating Alzheimer's disease, since undesirable side effects caused by the palladium radicals can occur in the organism. Consequently, boundary values at <5 ppm are normalized for the oral administration of pharmaceutical agents, see "Note for Guidance on Specification Limits for Residues of Metal Catalysts" CPMP/SWP/QWP/4446/00.

The object of the invention is therefore to indicate processes of the above-mentioned type with which the above-mentioned, normalized boundary values can be maintained.

SUMMARY OF THE INVENTION

According to the invention, a process for the production of the above-mentioned compounds with general formula (I) or (II) is proposed, whereby in a reaction step 1, racemic bromine narwedine (III) is debrominated with palladium (II) acetate and triphenylphosphine, in a reaction step 2, the reaction mixture that contains racemic narwedine (IV) is worked up under oxygen contact and converted into an enantiomerically pure narwedine (V), and whereby in a reaction step 3, enantiomerically pure galanthamine of general formula (I) with $R_1$ equal to $CH_3$ is obtained by reduction, and in a reaction step 4, compounds of general formula (I) are obtained by alkylation or dealkylation, or in a reaction step 4', compounds of general formula (II) are obtained by alkylation and dealkylation as well as subsequent salt formation.

As an alternative, according to the invention, a process for the production of the above-mentioned compounds with the general formula (I) or (II) is proposed, whereby in a reaction step 1, racemic bromine narwedine (III) is debrominated with palladium (II) acetate and triphenylphosphine, in a reaction step 2, the reaction mixture, which contains racemic narwedine (IV), is worked up with use of peroxides and converted into an enantiomerically pure narwedine (V), and whereby in a reaction step 3, enantiomerically pure galanthamine of general formula (I) with $R_1$ equal to $CH_3$ is obtained by reduction, and in a reaction step 4, compounds of general formula (I) are obtained by alkylation or dealkylation, or in a reaction step 4', compounds of general formula (II) are obtained by alkylation and dealkylation as well as subsequent salt formation.

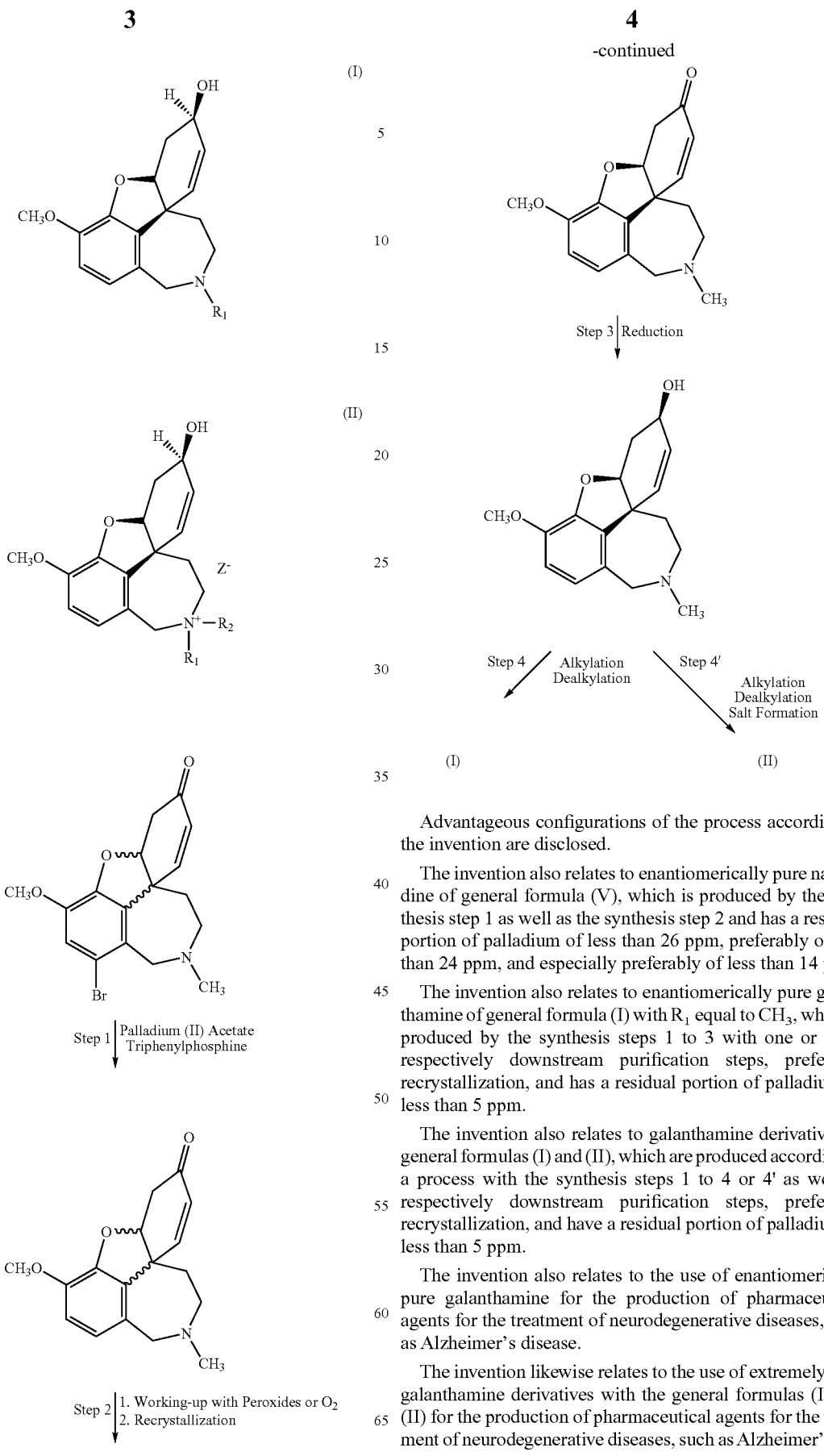

Advantageous configurations of the process according to the invention are disclosed.

The invention also relates to enantiomerically pure narwedine of general formula (V), which is produced by the synthesis step 1 as well as the synthesis step 2 and has a residual portion of palladium of less than 26 ppm, preferably of less than 24 ppm, and especially preferably of less than 14 ppm.

The invention also relates to enantiomerically pure galanthamine of general formula (I) with $R_1$ equal to $CH_3$, which is produced by the synthesis steps 1 to 3 with one or more respectively downstream purification steps, preferably recrystallization, and has a residual portion of palladium of less than 5 ppm.

The invention also relates to galanthamine derivatives of general formulas (I) and (II), which are produced according to a process with the synthesis steps 1 to 4 or 4' as well as respectively downstream purification steps, preferably recrystallization, and have a residual portion of palladium of less than 5 ppm.

The invention also relates to the use of enantiomerically pure galanthamine for the production of pharmaceutical agents for the treatment of neurodegenerative diseases, such as Alzheimer's disease.

The invention likewise relates to the use of extremely pure galanthamine derivatives with the general formulas (I) and (II) for the production of pharmaceutical agents for the treatment of neurodegenerative diseases, such as Alzheimer's disease.

DETAILED DESCRIPTION OF THE INVENTION

The invention is explained in more detail below based on the embodiments for implementing the invention, whereby reference is made to the process steps according to the reaction diagram:

Step 1: Racemic bromine narwedine of general formula (III) is taken up in DMF and mixed with $NaCO_2H$, $PPH_3$, palladium (II) acetate as well as sodium hydroxide. This reaction mixture is heated to 94° C. and kept at this temperature for six hours, whereby the reaction sequence is tracked by means of chromatography. Then, the reaction mixture is worked up, whereby DMF is distilled off, and the racemic narwedine (IV) is precipitated by adding water and is separated.

Step 2.1: The racemic narwedine (IV) that is obtained is taken up in a mixture of ethanol/triethylamine and mixed with activated carbon and a filter aid. The mixture is refluxed for one to four hours while being stirred intensively, whereby an air-nitrogen mixture is blown through the reactor with, for example, 5% by volume of oxygen. Surprisingly enough, it was found that by the treatment with activated carbon, on the one hand, and the oxygen contact, on the other hand, the reduction of the palladium portions of considerably above 95% in comparison to known, detectable amounts of palladium could be achieved. This is to be explained in more detail based on the following table:

|  | 1. Feedstock Pd (ppm) | 2. Feedstock Pd (ppm) | 3. Feedstock Pd (ppm) |
| --- | --- | --- | --- |
| Racemic Narwedine | 813 | 748 | 753 |
| (−)-Narwedine | 24 | 26 | 14 |

It can be seen from this tabular list that in the racemic narwedine mixture, palladium radicals of 748 to 813 ppm can be detected. Reaction end products with these portions of palladium are unsuitable for a further use for the production of a pharmaceutical agent. By the working-up of the reaction mixture with activated carbon according to the invention with simultaneous oxygen contact, the palladium catalyst is converted into an insoluble, oxidized form, so that a separation into a ppm range of less than 26, preferably of less than 24, and especially preferably of less than 14, is possible.

In an alternative process variant, the racemic narwedine (IV) that is obtained is also taken up in a mixture of ethanol/triethylamine and is mixed with activated carbon and a filter aid; however, this mixture is then slowly mixed with 0.1-1% by weight of hydrogen peroxide while being stirred intensively, and it is refluxed for one to four hours. Surprisingly enough, it was also found in this process variant that by the treatment with activated carbon, on the one hand, and the use of hydrogen peroxide, on the other hand, the palladium portion could be considerably reduced after filtration in comparison to the known detectable palladium portions. The measured values can be seen in the following table:

|  | 1. Feedstock Pd (ppm) | 2. Feedstock Pd (ppm) | 3. Feedstock Pd (ppm) |
| --- | --- | --- | --- |
| Racemic Narwedine | 800 | 810 | 763 |
| (−)-Narwedine (H2O2-Treated) | 22 | 24 | 16 |

In another process variant, the mixture that consists of racemic narwedine (IV), ethanol, triethylamine, activated carbon and a filter aid is mixed with 0.1-1% by weight of metachloroperbenzoic acid while being stirred intensively and refluxed for one to four hours.

Also in this process variant, it was found, surprisingly enough, that by the treatment with activated carbon, on the one hand, and the use of metachloroperbenzoic acid, on the other hand, the palladium portion can be significantly reduced in comparison to known detectable palladium portions after filtration. The determined values are cited in the following table:

|  | 1. Feedstock Pd (ppm) | 2. Feedstock Pd (ppm) | 3. Feedstock Pd (ppm) |
| --- | --- | --- | --- |
| Racemic Narwedine | 778 | 805 | 767 |
| (−)-Narwedine (MCPBA-Treated) | 20 | 23 | 18 |

Step 2.2: The reaction mixture that is obtained according to step 2.1 is cooled and inoculated with (−)narwedine crystals, so that enantiomerically pure (−)narwedine with general formula (V) is obtained.

Step 3: The enantiomerically pure (−)narwedine with the general formula (V) that is obtained after recrystallization, as described in WO-A-96/12692, is mixed with a one-molar solution of 1-selectride in THF, allowed to stir for one hour, mixed with ethanol, and concentrated by evaporation. Enantiomerically pure galanthamine of general formula (I) for $R_1=CH_3$ is obtained by the enantiomerically selective reduction. Residual portions of palladium of less than 5 ppm are achieved by recrystallization that is repeated one or more times. Therefore, according to synthesis step 2.1, by being worked up with oxygen or peroxide, the palladium catalyst is converted into an insoluble, oxidized form that can be easily separated by recrystallization during the course of the purification.

Step 4: The compound of general formula (I) with $R_1$ equal to $CH_3$ can be subjected to a dealkylation or another alkylation in order to introduce the radical $R_1$ or $R_2$ on the nitrogen atom.

Step 4': Step 4' is carried out analogously to Step 4 with the difference that another reaction is carried out with an acid, such as, for example, hydrobromide, to form pharmaceutically acceptable salts with counteranions Z", such as, for example, a bromide. Also, the compounds with the general formula (I) or (II) can, if necessary, further be purified by recrystallization, so that a residual portion of less than 5 ppm is achieved.

The above-mentioned embodiments were implemented such that $R_1$ or $R_2$ shows a substituent pattern, in which aliphatic carbon substituents have a number of carbons in the range of 1 to 6, and the aromatic radical aryl is selected from the group furyl, phenyl, pyridinyl, pyridazyl, pyrazinyl, pyrazolyl, imidazyl, and pyrazyl. This selection by way of example is, however, not to be considered as a limitation of the scope of protection.

The pharmacological action of the compounds according to general formulas (I) and (II) can be substantiated based on the measured $IC^{50}$ values, since the latter represent any concentrations in which a 50% inhibition of the acetylcholinesterase (AChEI) or the butyrylcholinesterase (BuCHEI) occurs. Satisfactory inhibiting values—see following overview—are in addition an indication of the fact that the compounds of general formula (I) or (II) are suitable for the production of pharmaceutical agents for the treatment of neurodegenerative diseases, such as Alzheimer's disease.

| EXAMPLE | IMAGE OF THE FORMULA | RESEARCH CODE | IC$_{50}$ AChEI | IC$_{50}$ BuChEI |
|---|---|---|---|---|
| 1 | | SPH-1097 | 200 | 2.6 |
| 2 | | SPH-1071 | 49 | 14 |
| 3 | | SPH-1054 | 12 | 0.2 |
| 4 | | SPH-1075 | 63 | 10 |
| 5 | | SPH-1080 | 200 | 56 |

-continued

| EXAMPLE | IMAGE OF THE FORMULA | RESEARCH CODE | IC$_{50}$ AChEI | IC$_{50}$ BuChEI |
|---|---|---|---|---|
| 6 | (galantamine derivative with Br, OCH₃, OH, and N-CH₂CN substituent) | SPH-1069 | 200 | 70 |
| 7 | (galantamine derivative with Br, OCH₃, OH, and N-CH₂C(O)NH₂ substituent) | SPH-1081 | 200 | 15 |
| 8 | (galantamine derivative with Br, OCH₃, OH, and N-CH₂CH₂-morpholine substituent) | SPH-1078 | 200 | 4.4 |
| 9 | (galantamine derivative with Br, OCH₃, OH, and N-(CH₂)₃-piperidine substituent) | SPH-1106 | 23 | 3.3 |
| 10 | (galantamine derivative with Br, OCH₃, OH, and N-C(O)C(O)OCH₂CH₃ substituent) | SPH-1070 | 32.5 | 11 |

-continued

| EXAMPLE | IMAGE OF THE FORMULA | RESEARCH CODE | IC$_{50}$ AChEI | IC$_{50}$ BuChEI |
|---|---|---|---|---|
| 11 | | SPH-1072 | 200 | 200 |
| 12 | | SPH-1082 | 200 | 200 |
| 13 | | SPH-1090 | 200 | 200 |
| 14 | | SPH-1095 | 34 | 6.35 |
| 15 | | SPH-1096 | 15 | 19 |

-continued

| EXAMPLE | IMAGE OF THE FORMULA | RESEARCH CODE | IC$_{50}$ AChEI | IC$_{50}$ BuChEI |
|---|---|---|---|---|
| 16 | | SPH-1089 | 200 | 200 |
| 17 | | SPH-1099 | 37 | 200 |
| 18 | | SPH-1098 | 13 | 7 |
| 19 | | SPH-1023 | 60 | 8 |
| 20 | | SPH-1098 (rac) | 13 (rac) | 7 (rac) |

-continued

| EXAMPLE | IMAGE OF THE FORMULA | RESEARCH CODE | IC$_{50}$ AChEI | IC$_{50}$ BuChEI |
|---|---|---|---|---|
| 21 | | SPH-1144 | 6.2 | 3.6 |
| 22 | | SPH-1019 | 30 | 5.6 |
| 23 | | SPH-1052 | 200 | 200 |
| 24 | | SPH-1058 | 1.35 | 1.6 |
| 25 | | SPH-1140 | 3.1 | 2.5 |

-continued

| EXAMPLE | IMAGE OF THE FORMULA | RESEARCH CODE | IC$_{50}$ AChEI | IC$_{50}$ BuChEI |
|---|---|---|---|---|
| 26 | | SPH-1195 | 24.5 | 7.5 |
| 27 | | SPH-1329 | 2.9 | 0.9 |

In summary, it can be stated that the palladium catalyst that is used can be converted into an insoluble oxide form and can be separated in a simple way by the working-up according to the invention of a debrominated narwedine that is obtained by palladium catalysis, namely by contact with oxygen or peroxides. By this working-up of the reaction mixture, which was completely in line with the safety regulations, it was possible, surprisingly enough, to reduce the palladium radicals to below 5 ppm, so that extremely pure galanthamine or extremely pure galanthamine derivatives could be obtained, which could (can) be used directly in the production of pharmaceutical agents, such as, for example, those for the treatment of Alzheimer's disease.

The invention claimed is:

1. A process for producing 4a,5,9,10,11,12-hexahydro-6H-benzofuro[3a,3,2-ef][2]benzazepine and its derivatives with formulas I and II:

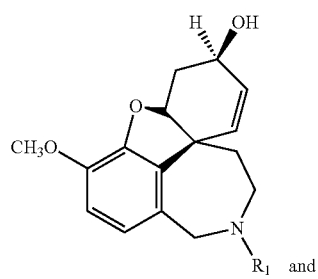
(I)

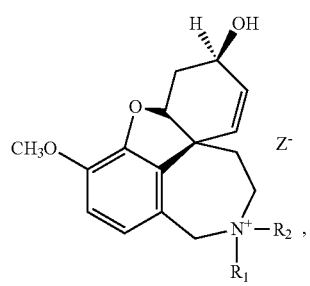
(II)

or salts thereof,
wherein,
$R_1$ is selected from the group consisting of: hydrogen, hydroxy, alkoxy, low alkyl, low alkyl substituted by at least one halogen, low alkenyl, low alkinyl, aryl, aralkyl, aryloxyalkyl, formyl, alkylcarbonyl, arylcarbonyl, aralkylcarbonyl, alkyloxycarbonyl, aryloxycarbonyl, aralkyloxycarbonyl, alkylsulfonyl, aralkylsulfonyl, and arylsulfonyl, $R_2$ is selected from the group consisting of: hydrogen, formyl, alkyl, alkenyl, aryl, aralkyl, alkylcarbonyl, arylcarbonyl, aralkylcarbonyl, alkyloxycarbonyl, aryloxycarbonyl, aralkyloxycarbonyl, alkylsulfonyl, arylsulfonyl and aralkylsulfonyl, and $Z^-$ is an anion of a pharmaceutically acceptable organic acid or an inorganic anion, said process comprising:
reaction step 1, debrominating racemic bromine narwedine with palladium (II) acetate and triphenylphosphine to obtain racemic narwedine, reaction step 2, contacting the racemic narwedine with oxygen and converting the racemic narwedine into an enantiomerically pure narwedine, reaction step 3, reducing the enantiomerically pure narwedine to obtain enantiomerically pure galanthamine of formula (I) with $R_1$ equal to $CH_3$, and reaction step 4, alkylating or dealkylating the galanthamine to obtain compounds of formula (I), or reaction step 4', alkylating or dealkylating the galanthamine and subsequently forming a salt to obtain compounds of formula (II).

2. The process according to claim 1, wherein the reaction step 2 is carried out with an air-nitrogen mixture.

3. The process according to claim 2, wherein the air-nitrogen mixture contains 0.2 to 20% by volume of oxygen.

4. The process according to claim 1, wherein the reaction step 2 is carried out in the presence of activated carbon.

5. The process according to claim 1, further comprising one or more purification step(s) downstream to the reaction step 3 and/or the reaction step 4.

6. Enantiomerically pure narwedine produced by the reaction step 1 and the reaction step 2 according to claim 1, wherein the narwedine has a residual portion of palladium of less than 26 ppm.

7. Enantiomerically pure galanthamine of formula (I), wherein $R_1$ is $CH_3$, produced by the reaction steps 1 to 3 and the one or more downstream purification steps according to claim 5, wherein the galanthamine has a residual portion of palladium of less than 5 ppm.

8. Galanthamine derivatives of formulas (I) and (II), produced by the reaction steps 1 to 4 and the one or more downstream purification steps according to claim 5, wherein the galanthamine derivative has a residual portion of palladium of less than 5 ppm.

9. A process for producing 4a,5,9,10,11,12-hexahydro-6H-benzofuro[3a,3,2-ef][2]benzazepine and its derivatives with formulas I and II:

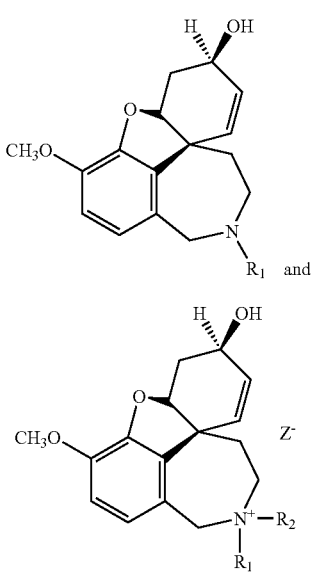

or salts thereof,
wherein,
$R_1$ is selected from the group consisting of: hydrogen, hydroxy, alkoxy, low alkyl, low alkyl substituted by at least one halogen, low alkenyl, low alkinyl, aryl, aralkyl, aryloxyalkyl, formyl, alkylcarbonyl, arylcarbonyl, aralkylcarbonyl, alkyloxycarbonyl, aryloxycarbonyl, aralkyloxycarbonyl, alkylsulfonyl, aralkylsulfonyl, and arylsulfonyl, $R_2$ is selected from the group consisting of: hydrogen, formyl, alkyl, alkenyl, aryl, aralkyl, alkylcarbonyl, arylcarbonyl, aralkylcarbonyl, alkyloxycarbonyl, aryloxycarbonyl, aralkyloxycarbonyl, alkylsulfonyl, arylsulfonyl and aralkylsulfonyl, and $Z^-$ is an anion of a pharmaceutically acceptable organic acid or an inorganic anion, said process comprising:
reaction step 1, debrominating racemic bromine narwedine with palladium (II) acetate and triphenylphosphine to obtain racemic narwedine, reaction step 2, contacting the racemic narwedine with peroxides and converting the racemic narwedine into an enantiomerically pure narwedine reaction step 3, reducing the enantiomerically pure narwedine to obtain enantiomerically pure galanthamine of formula (I) with $R_1$ equal to $CH_3$, and reaction step 4, alkylating or dealkylating the galanthamine to obtain compounds of formula (I), or reaction step 4', alkylating or dealkylating the galanthamine and subsequently forming a salt to obtain compounds of formula (II).

10. The process according to claim 9, wherein in reaction step 2, the peroxide is inorganic peroxide.

11. The process according to claim 9, wherein in the reaction step 2, the peroxide is organic peroxide.

12. The process according to claim 9, wherein the reaction step 2 is carried out in the presence of activated carbon.

13. The process according to claim 9, further comprising one or more purification step(s) downstream to the reaction step 3 and/or the reaction step 4.

14. Enantiomerically pure narwedine produced by the reaction step 1 and the reaction step 2 according to claim 9, wherein the narwedine has a residual portion of palladium of less than 26 ppm.

15. Enantiomerically pure galanthamine of formula (I), wherein $R_1$ is $CH_3$, produced by the reaction steps 1 to 3 and the one or more downstream purification steps according to claim 13, wherein the galanthamine has a residual portion of palladium of less than 5 ppm.

16. Galanthamine derivatives of formulas (I) and (II), produced by the reaction steps 1 to 4 and the one or more downstream purification steps according to claim 13, wherein the galanthamine derivative has a residual portion of palladium of less than 5 ppm.

17. The process according to claim 5, wherein the one or more purification step(s) comprise recrystallization.

18. The process according to claim 6, wherein the narwedine has a residual portion of palladium of less than 14 ppm.

19. The process according to claim 10, wherein the peroxide is hydrogen peroxide.

20. The process according to claim 11, wherein the peroxide is metachloroperbenzoic acid.

21. The process according to claim 13, wherein the one or more purification step(s) comprise recrystallization.

22. The process according to claim 14, wherein the narwedine has a residual portion of palladium of less than 14 ppm.

* * * * *